(12) United States Patent
Tsuruta et al.

(10) Patent No.: US 10,036,887 B2
(45) Date of Patent: Jul. 31, 2018

(54) OPTICAL FIBER SCANNER, ILLUMINATION SYSTEM, AND OBSERVATION APPARATUS

(71) Applicant: OLYMPUS CORPORATION, Tokyo (JP)

(72) Inventors: Hiroshi Tsuruta, Kanagawa (JP); Yasuaki Kasai, Saitama (JP)

(73) Assignee: OLYMPUS CORPORATION, Tokyo (JP)

( * ) Notice: Subject to any disclaimer, the term of this patent is extended or adjusted under 35 U.S.C. 154(b) by 155 days.

(21) Appl. No.: 15/089,644

(22) Filed: Apr. 4, 2016

(65) Prior Publication Data

US 2016/0216510 A1 Jul. 28, 2016

Related U.S. Application Data

(63) Continuation of application No. PCT/JP2014/075729, filed on Sep. 26, 2014.

(30) Foreign Application Priority Data

Oct. 8, 2013 (JP) .................. 2013-210853

(51) Int. Cl.
*G02B 26/10* (2006.01)
*G01N 21/47* (2006.01)
(Continued)

(52) U.S. Cl.
CPC ........ *G02B 26/103* (2013.01); *A61B 1/00172* (2013.01); *A61B 1/07* (2013.01);
(Continued)

(58) Field of Classification Search
CPC .............. G02B 26/103; G02B 6/3578; G02B 2006/0098; A61B 1/07; A61B 1/00172;
(Continued)

(56) References Cited

U.S. PATENT DOCUMENTS

| 7,129,472 B1 | 10/2006 | Okawa et al. |
| 8,169,466 B2 * | 5/2012 | Iketani ................ A61B 1/0638 348/42 |
| 2013/0345508 A1 | 12/2013 | Akui |

FOREIGN PATENT DOCUMENTS

| CN | 104620156 A | 5/2015 |
| EP | 2 803 312 A1 | 11/2014 |

(Continued)

OTHER PUBLICATIONS

International Search Report dated Dec. 16, 2014 issued in PCT/JP2014/075729.

(Continued)

*Primary Examiner* — Tony Ko
(74) *Attorney, Agent, or Firm* — Scully, Scott, Murphy & Presser, P.C.

(57) ABSTRACT

An optical fiber scanner is provided with an illumination optical fiber that guides light and emits the light from a distal end thereof; a plurality of piezoelectric elements that are secured on a side surface of the illumination optical fiber, that have polarizations in radial directions of the illumination optical fiber, and that vibrate the illumination optical fiber when an alternating voltage is applied in the polarization directions; and a vibration suppressing part that suppresses vibrations in the radial directions generated at a position of the illumination optical fiber away from the piezoelectric elements toward a base end.

7 Claims, 17 Drawing Sheets

(51) Int. Cl.
  *G01N 21/64* (2006.01)
  *G01J 1/04* (2006.01)
  *G02B 6/35* (2006.01)
  *A61B 1/00* (2006.01)
  *A61B 1/07* (2006.01)
  *G02B 6/00* (2006.01)
(52) U.S. Cl.
  CPC .......... *G01J 1/0403* (2013.01); *G01N 21/474* (2013.01); *G01N 21/6456* (2013.01); *G02B 6/3578* (2013.01); *G01N 2021/4742* (2013.01); *G01N 2021/6465* (2013.01); *G01N 2021/6484* (2013.01); *G02B 2006/0098* (2013.01)
(58) Field of Classification Search
  CPC . G01J 1/0403; G01N 21/6456; G01N 21/474; G01N 2021/6484; G01N 2021/6465; G01N 2021/4742
  See application file for complete search history.

(56) References Cited

FOREIGN PATENT DOCUMENTS

| JP | 2008-504557 A | 2/2008 |
| WO | WO 2006/004743 A2 | 1/2006 |
| WO | WO 2012/073958 A1 | 6/2012 |
| WO | 2013/105329 A1 | 7/2016 |

OTHER PUBLICATIONS

Extended Supplementary European Search Report dated Jun. 26, 2017 in European Patent Application No. 14 85 2416.8.

* cited by examiner

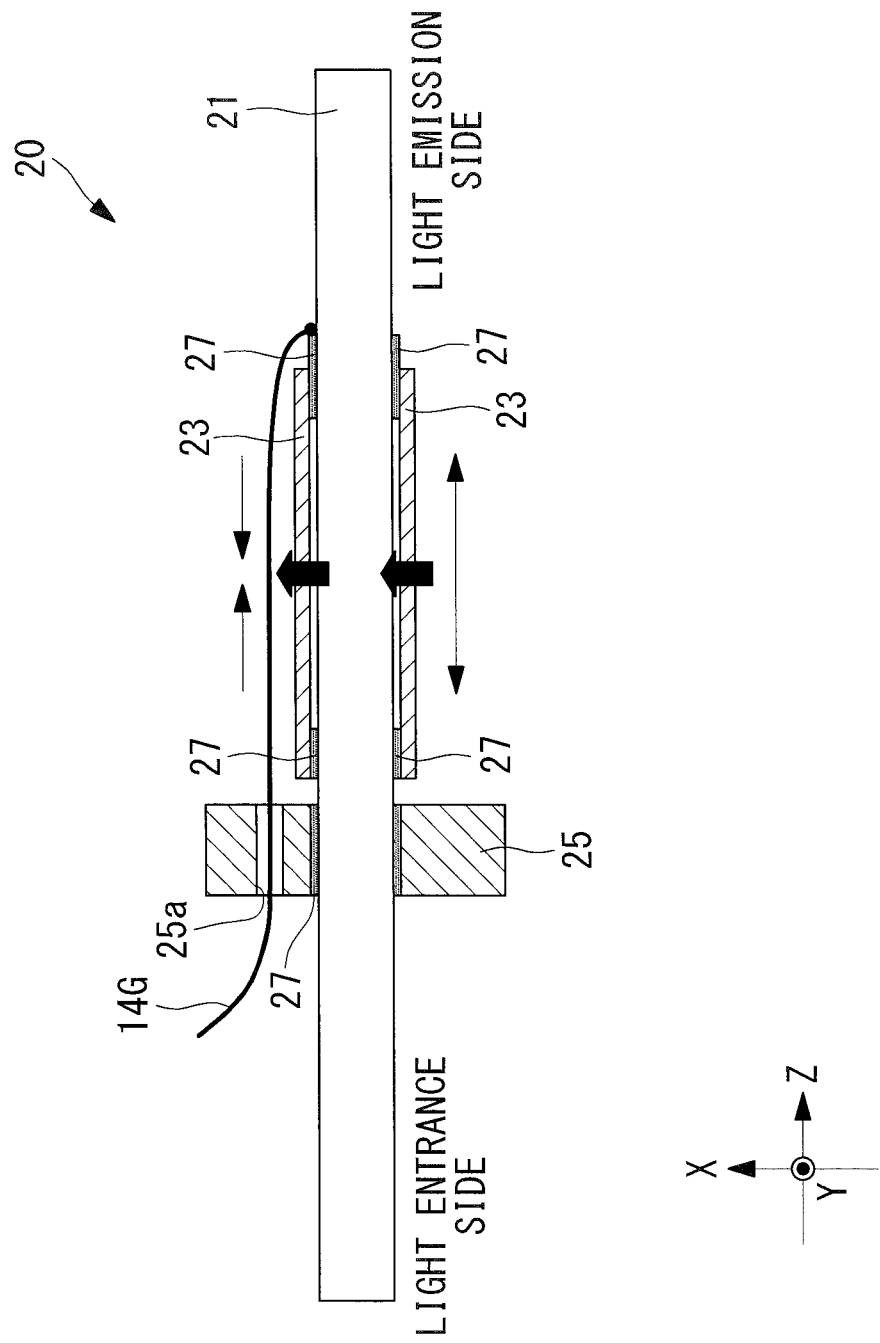

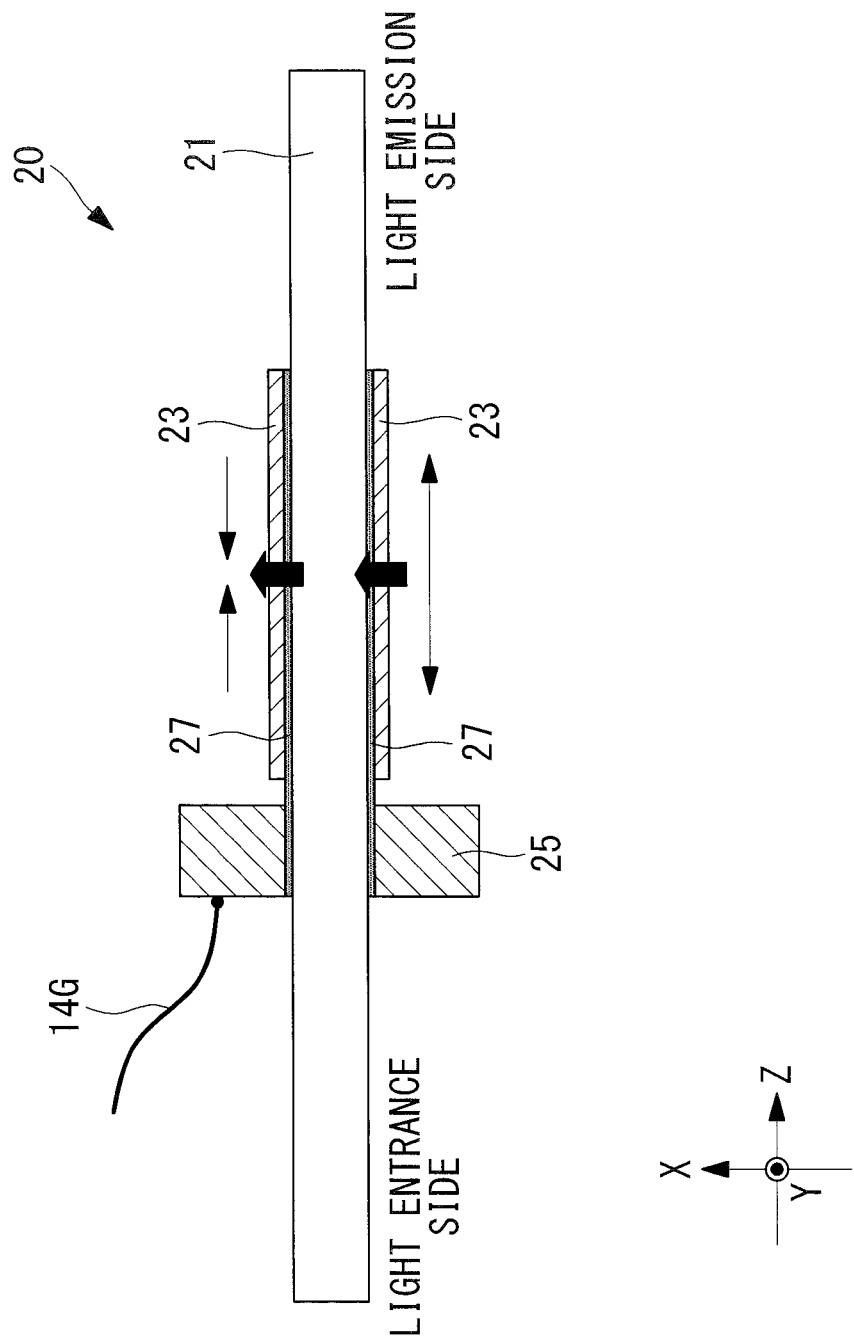

US 10,036,887 B2

OPTICAL FIBER SCANNER, ILLUMINATION SYSTEM, AND OBSERVATION APPARATUS

CROSS-REFERENCE TO RELATED APPLICATIONS

This is a continuation of International Application PCT/JP2014/075729 which is hereby incorporated by reference herein in its entirety.

This application is based on Japanese Patent Application No. 2013-210853, the contents of which are incorporated herein by reference.

TECHNICAL FIELD

The present invention relates to an optical fiber scanner, an illumination system, and an observation apparatus.

BACKGROUND ART

There are known optical fiber scanners for scanning an optical fiber (for example, see PTL 1). An optical fiber scanner described in PTL 1 is provided with a cylindrical lead-zirconate-titanate (PZT) actuator, an optical fiber that is scanned by the PZT actuator in one direction or in two directions intersecting one another, and a connecting member that supports the optical fiber with a cantilever arm, in which the PZT actuator is driven to generate bending vibrations, and thus the bending vibrations are transferred to the optical fiber via the connecting member. Furthermore, the optical fiber scanner described in PTL 1 combines two-directional bending vibrations generated by the PZT actuator in an X-axis direction and a Y-axis direction, in consideration of the amplitudes and phases, thereby making it possible to spirally scan the optical fiber.

CITATION LIST

Patent Literature

{PTL 1} Japanese Translation of PCT International Application, Publication No. 2008-504557

SUMMARY OF INVENTION

Solution to Problem

According to a first aspect, the present invention provides an optical fiber scanner including: an optical fiber that guides light and emits the light from a distal end thereof; a plurality of piezoelectric elements that are secured on a side surface of the optical fiber, that have polarizations in radial directions of the optical fiber, and that vibrate the optical fiber when an alternating voltage is applied in the polarization directions; and a vibration suppressing part that suppresses vibrations in the radial directions generated at a position of the optical fiber away from the piezoelectric elements toward a base end.

BRIEF DESCRIPTION OF DRAWINGS

FIG. 2A is a plan view of an optical fiber scanner shown in FIG. 1, viewed in a radial direction of an illumination optical fiber.

FIG. 4A is a plan view of the optical fiber scanner shown in FIG. 3, viewed in a radial direction of an illumination optical fiber.

DESCRIPTION OF EMBODIMENT

An optical fiber scanner, an illumination system, and an observation apparatus according to one embodiment of the present invention will be described below with reference to the drawings.

Figure 1:
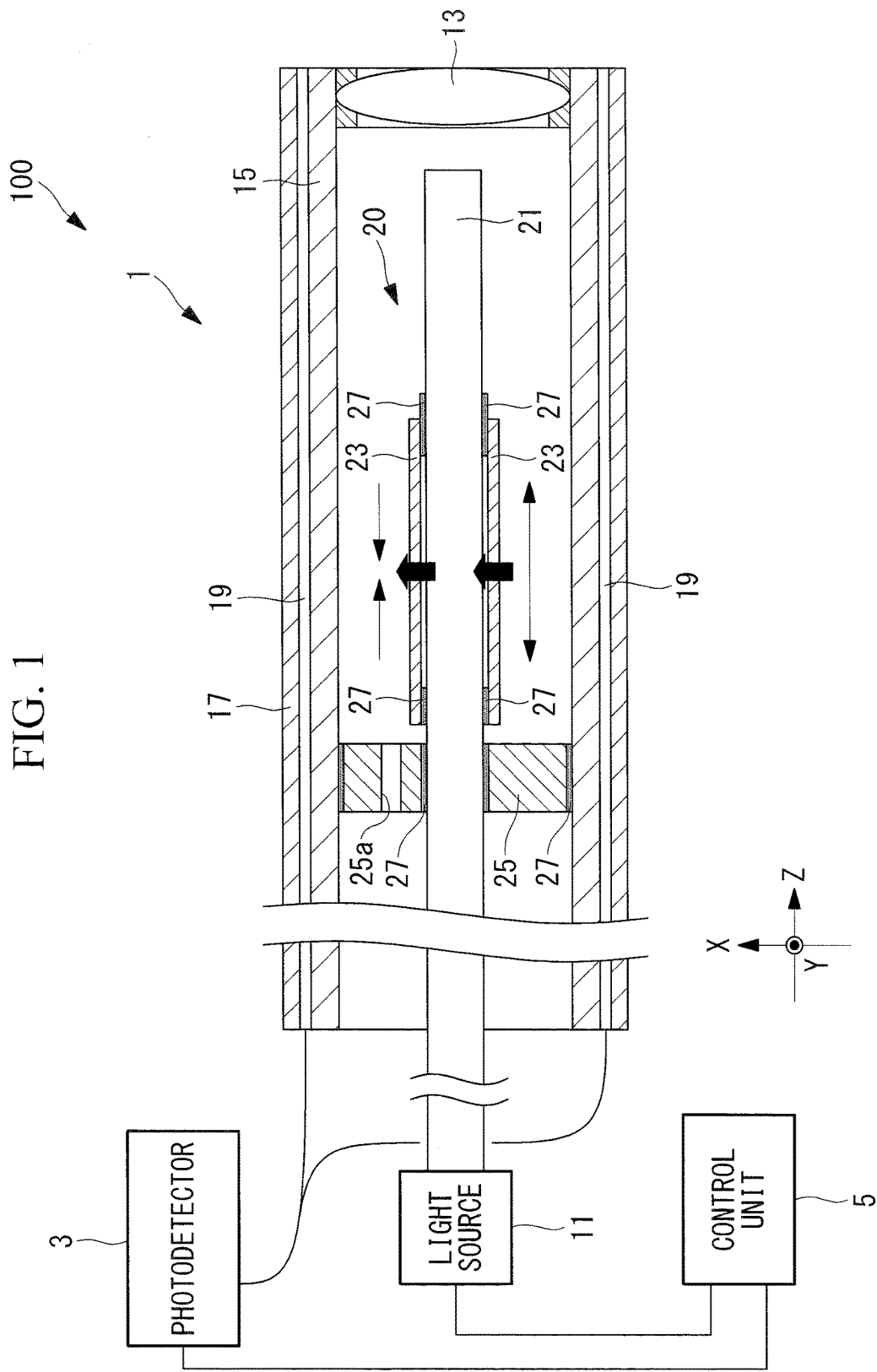
FIG. 1 is a view showing, in outline, the configuration of an observation apparatus according to one embodiment of the present invention.

As shown in FIG. 1, an observation apparatus 100 of this embodiment is provided with an illumination system 1 that radiates illumination light onto an object, a photodetector (photodetection unit) 3 that detects return light returning from the object onto which the illumination light has been radiated, and a control unit 5 that controls the illumination system 1 and the photodetector 3.

The illumination system 1 is provided with a light source 11 that produces illumination light, an optical fiber scanner 20 that has an illumination optical fiber 21 for guiding the illumination light produced in the light source 11 and emitting the illumination light from a distal end thereof, a condensing lens 13 that condenses the illumination light emitted from the illumination optical fiber 21, an elongated cylindrical external cylinder 15 that accommodates the optical fiber scanner 20 and the condensing lens 13, a coating member 17 that coats an outer circumferential surface of the external cylinder 15, and a plurality of detection optical fibers 19 that are disposed between the external cylinder 15 and the coating member 17 and that guide return light from the object to the photodetector 3.

The light source 11 and the photodetector 3 are disposed, outside the external cylinder 15, close to one end of the external cylinder 15 in the longitudinal direction thereof. In the longitudinal direction of the external cylinder 15, the end of the external cylinder 15 close to the light source 11 and the photodetector 3 is referred to as a base end, and the other end thereof is referred to as a distal end.

Figure 2B:
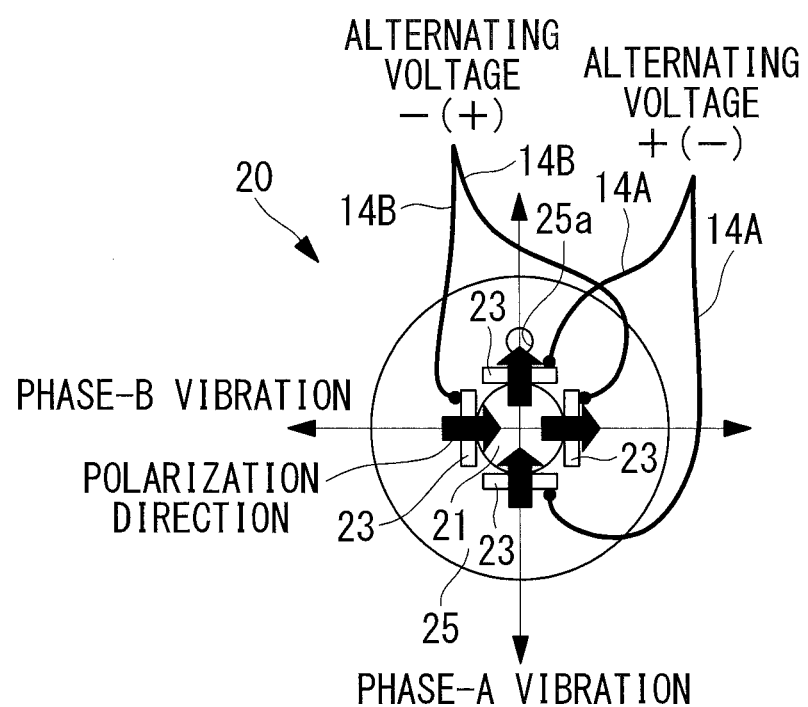
FIG. 2B is a plan view of FIG. 2A, viewed in the longitudinal direction of the illumination optical fiber.

As shown in FIGS. 2A and 2B, the optical fiber scanner 20 is provided with the illumination optical fiber 21, four piezoelectric elements 23 that are secured on a side surface of the illumination optical fiber 21, and a securing part (vibration suppressing part) 25 that secures the illumination optical fiber 21 to the external cylinder 15.

The illumination optical fiber 21 has an elongated cylindrical shape made from a glass material and is disposed along the longitudinal direction of the external cylinder 15. Furthermore, one end of the illumination optical fiber 21 is connected to the light source 11 outside the base end of the external cylinder 15, and the other end of the illumination optical fiber 21 is disposed inside the external cylinder 15 in the vicinity of the distal end of the external cylinder 15. The illumination optical fiber 21 guides light entering one end thereof from the light source 11 and emits the light from the other end thereof.

The piezoelectric elements 23 are made from a piezoceramic material, such as lead zirconate titanate (PZT), for example, and are each formed into an elongated-plate shape. Furthermore, in each of the piezoelectric elements 23, a front surface is positively polarized, and a back surface is negatively polarized, thus being polarized in the direction from the positive pole to the negative pole, i.e., in a plate-thickness direction.

The four piezoelectric elements 23 are arranged, at the same position in the longitudinal direction of the illumination optical fiber 21, at intervals of approximately 90 degrees in the circumferential direction and are secured such that the directions of their polarizations match radial directions of the illumination optical fiber 21. Furthermore, a pair of piezoelectric elements 23 that face each other in a radial direction of the illumination optical fiber 21 (hereinafter, simply referred to as "a pair of piezoelectric elements 23") are arranged such that the directions of their polarizations point in the same direction, as indicated by arrows in FIG. 2B.

Furthermore, the piezoelectric elements 23 are each bonded, in the vicinities of both ends thereof in the longitudinal direction, to the side surface of the illumination optical fiber 21 by means of conductive epoxy adhesives (hereinafter, simply referred to as "adhesives", vibration transferring parts) 27. The adhesives 27 transfer the vibrations of the piezoelectric elements 23 to the illumination optical fiber 21.

Because the adhesives 27 are electrically joined to back-surface electrodes of the four piezoelectric elements 23, the adhesives 27 can function as a common GND when the piezoelectric elements 23 are driven. Accordingly, a driving lead wire (GND) 14G is joined to one of the piezoelectric elements 23 via the adhesive 27 that is applied to the end of the corresponding piezoelectric element 23 close to the distal end of the illumination optical fiber 21.

Driving lead wires 14A that form phase A are joined, via conductive adhesives, to electrode surfaces of one pair of piezoelectric elements 23 among the four piezoelectric elements 23. Driving lead wires 14B that form phase B are joined, via conductive adhesives, to electrode surfaces of the other pair of piezoelectric elements 23.

When an alternating voltage is applied in the polarization direction through the lead wires 14A or the lead wires 14B, the piezoelectric elements 23 generate vibrations expanding and contracting in a direction perpendicular to the polarization directions thereof (transverse effect). Furthermore, the pair of piezoelectric elements 23 expand and contract such that one of them expands at the same time as the other contracts. Accordingly, the pair of piezoelectric elements 23 transfer the vibrations to the illumination optical fiber 21 via the adhesives 27, thereby making it possible to vibrate the distal end of the illumination optical fiber 21 in a direction intersecting the longitudinal direction.

The securing part 25 is made from a metal material, such as stainless steel, and is formed into an annular shape. A through hole 25a for allowing the lead wire 14G to pass therethrough is formed in the securing part 25. As in the piezoelectric elements 23, the outer circumferential surface of the securing part 25 is bonded to the inner wall of the external cylinder 15 by means of a conductive epoxy adhesive 27, and the inner circumferential surface of the securing part 25 is bonded to the side surface of the illumination optical fiber 21 by means of a conductive epoxy adhesive 27.

The securing part 25 is secured at a position of the illumination optical fiber 21 away from the piezoelectric elements 23 toward the base end and is capable of suppressing radial vibrations generated at this position of the illumination optical fiber 21. It is desirable that the securing part 25 be located away from the piezoelectric elements 23 so as not to hinder at least expansion and contraction of the piezoelectric elements 23 in directions intersecting the polarization directions thereof.

The condensing lens 13 is provided at the distal end of the external cylinder 15 in the longitudinal direction, condenses illumination light from the illumination optical fiber 21, and causes the illumination light to be emitted from the distal end of the external cylinder 15.

The detection optical fibers 19 each have an elongated cylindrical shape made from a glass material and are disposed along the longitudinal direction of the external cylinder 15. The detection optical fibers 19 are arranged so as to be spaced from each other in the circumferential direction of the external cylinder 15. Furthermore, one end of each detection optical fiber 19 is disposed at the distal end of the external cylinder 15, and the other end thereof is connected to the photodetector 3, so that the detection optical fiber 19 guides return light entering the end thereof to the photodetector 3.

In addition to controlling the illumination system 1 and the photodetector 3, the control unit 5 converts, when return light is detected by the photodetector 3, the return light into an electrical signal corresponding to the brightness thereof. Furthermore, the control unit 5 can read information about scanning positions of illumination light scanned by the optical fiber scanner 20 (scanning position information) and can generate image information by associating the scanning position information with an electrical signal of return light.

The operation of the thus-configured optical fiber scanner 20, illumination system 1, and observation apparatus 100 will be described.

In order to observe an object by using the optical fiber scanner 20, the illumination system 1, and the observation apparatus 100 of this embodiment, the distal end of the external cylinder 15 is first disposed pointing toward the object, and illumination light is produced in the light source 11. The illumination light produced in the light source 11 is guided by the illumination optical fiber 21, thus being emitted from the distal end thereof, and is radiated onto the object by the condensing lens 13.

When return light, such as reflected light and fluorescence, is produced in the object irradiated with the illumination light, the return light is received and guided by the detection optical fibers 19 and is detected by the photodetector 3. Then, the control unit 5 converts the return light into an electrical signal, associates the electrical signal with scanning position information of the optical fiber scanner 20, and converts them into image information. Accordingly, it is possible to acquire an image of the object irradiated with the illumination light.

Next, a description will be given of scanning of illumination light with the optical fiber scanner 20.

In order to scan illumination light with the optical fiber scanner 20, the illumination optical fiber 21 is first excited to have a bending resonant frequency at which the vicinities of the ends of the piezoelectric elements 23 closer to the distal end of the illumination optical fiber 21 serve as nodes, and the vicinity of the distal end of the illumination optical fiber 21 serves as an antinode.

When an alternating voltage corresponding to the bending resonant frequency is applied to one pair of piezoelectric elements 23 (hereinafter, referred to as phase-A piezoelectric elements 23), the distal end of the illumination optical fiber 21 can be vibrated in one direction (for example, referred to as an X-axis (phase-A) direction) intersecting the longitudinal direction by the phase-A piezoelectric elements 23 to which the alternating voltage has been applied.

In the same way, when an alternating voltage corresponding to the bending resonant frequency is applied to the other pair of piezoelectric elements 23 (hereinafter, referred to as phase-B piezoelectric elements 23), the distal end of the illumination optical fiber 21 can be vibrated in one direction (for example, a Y-axis (phase-B) direction) intersecting the X-axis direction by the phase-B piezoelectric elements 23 to which the alternating voltage has been applied.

When vibrations in the X-axis direction caused by the phase-A piezoelectric elements 23 and vibrations in the Y-axis direction caused by the phase-B piezoelectric elements 23 are simultaneously generated, and the phases of alternating signals applied to the phase-A piezoelectric elements 23 and the phase-B piezoelectric elements 23 are shifted by $\pi/2$, the vibrations of the distal end of the illumination optical fiber 21 follow a circular trajectory. With the vibrations of the distal end of the illumination optical fiber 21 following the circular trajectory, when the magnitudes of the alternating voltages applied to the phase-A piezoelectric elements 23 and the phase-B piezoelectric elements 23 are gradually increased and decreased (voltage modulation), the distal end of the illumination optical fiber 21 vibrates in a spiral manner. Accordingly, illumination light emitted from the distal end of the illumination optical fiber 21 can be spirally scanned on the object.

In this case, the securing part 25 suppresses the radial vibrations generated at the position of the illumination optical fiber 21 closer to the base end than the piezoelectric elements 23 are, thereby making it possible to form a node at the base end of the illumination optical fiber 21 and to prevent bending vibrations generated in the piezoelectric elements 23 from escaping toward the base end of the illumination optical fiber 21.

Even if the vibrations escape from the piezoelectric elements 23 toward the base end of the illumination optical fiber 21, it is possible to avoid a situation in which the vibrations return after being changed in shape by being affected in some way. Accordingly, the shape of the vibrations of the piezoelectric elements 23 and the vibrations of the illumination optical fiber 21 can be prevented from becoming unstable.

By forming the space between the piezoelectric elements 23 and the position at which the illumination optical fiber 21 is secured by the securing part 25, the piezoelectric elements 23 can be made to easily expand and contract in the longitudinal direction of the illumination optical fiber 21 without being obstructed by the securing part 25. Accordingly, a situation in which the vibrations of the piezoelectric elements 23 themselves are disturbed by the securing part 25, thus making it difficult to transfer the vibrations to the illumination optical fiber 21, can be prevented.

Therefore, according to the optical fiber scanner 20 of this embodiment, the illumination optical fiber 21 is made to stably generate bending vibrations, thus making it possible to perform stable spiral scanning on the object. Furthermore, according to the illumination system 1 of this embodiment, light produced in the light source 11 can be accurately scanned and radiated onto a desired position of the object. Furthermore, according to the observation apparatus 100 of this embodiment, it is possible to acquire image information of a desired observation region of the object.

This embodiment can be modified as follows.

Figure 3:
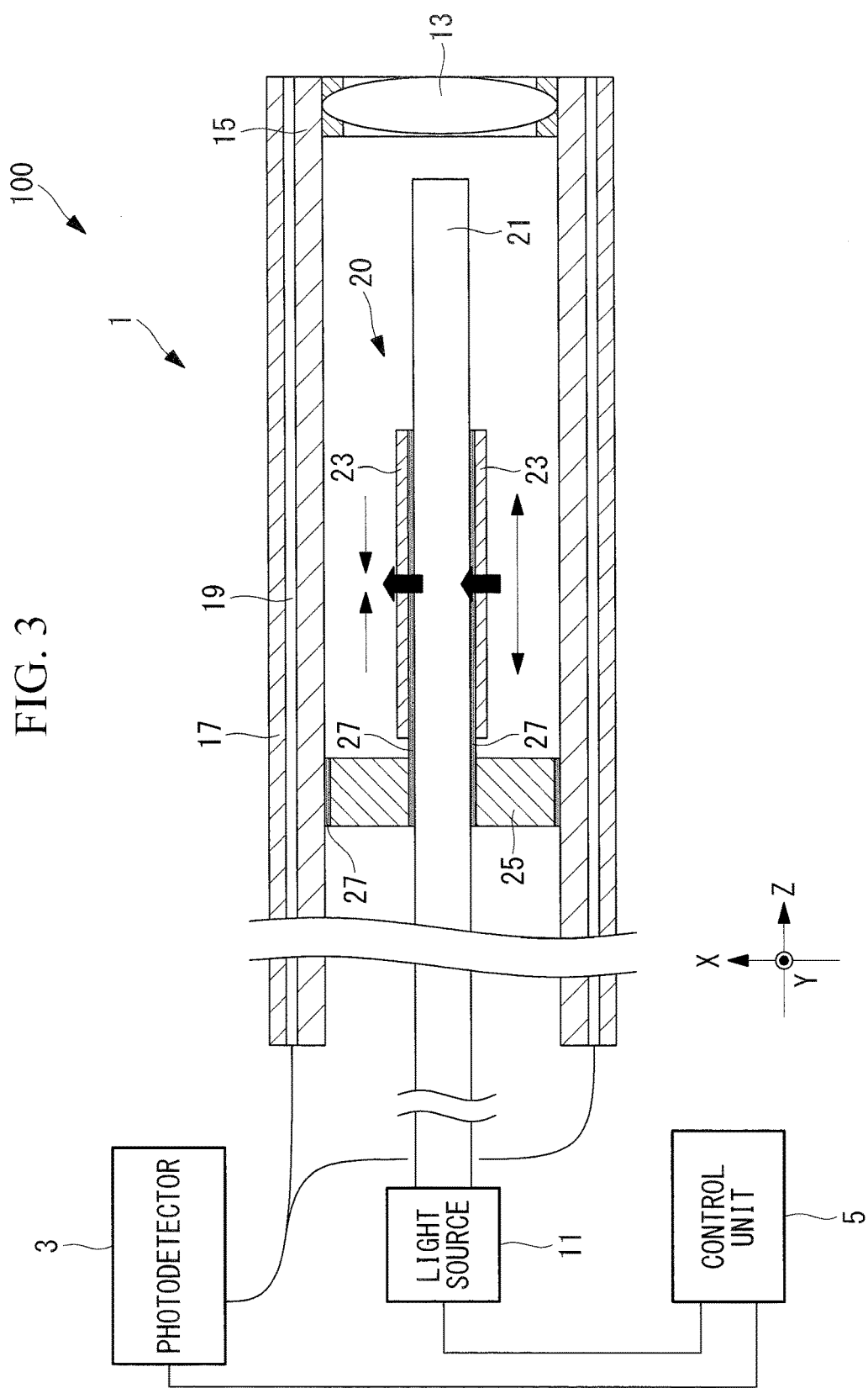
FIG. 3 is a view showing, in outline, the configuration of an optical fiber scanner according to a first modification of the embodiment of the present invention.

In this embodiment, the vicinities of both ends of the piezoelectric elements 23 in the longitudinal direction are bonded to the side surface of the illumination optical fiber 21 by means of the adhesives 27; however, in a first modification, as shown in FIG. 3, the piezoelectric elements 23 may be bonded over the entire length thereof in the longitudinal direction to the side surface of the illumination optical fiber 21 by means of the adhesives 27.

In this case, the adhesives 27 may be continuously filled in spaces from the piezoelectric elements 23 to the securing part 25 in the longitudinal direction of the illumination optical fiber 21, including the space between the piezoelectric elements 23 and the securing part 25.

By doing so, it is possible to improve the transfer efficiency of vibrations transferred from the piezoelectric elements 23 to the illumination optical fiber 21.

Figure 4B:
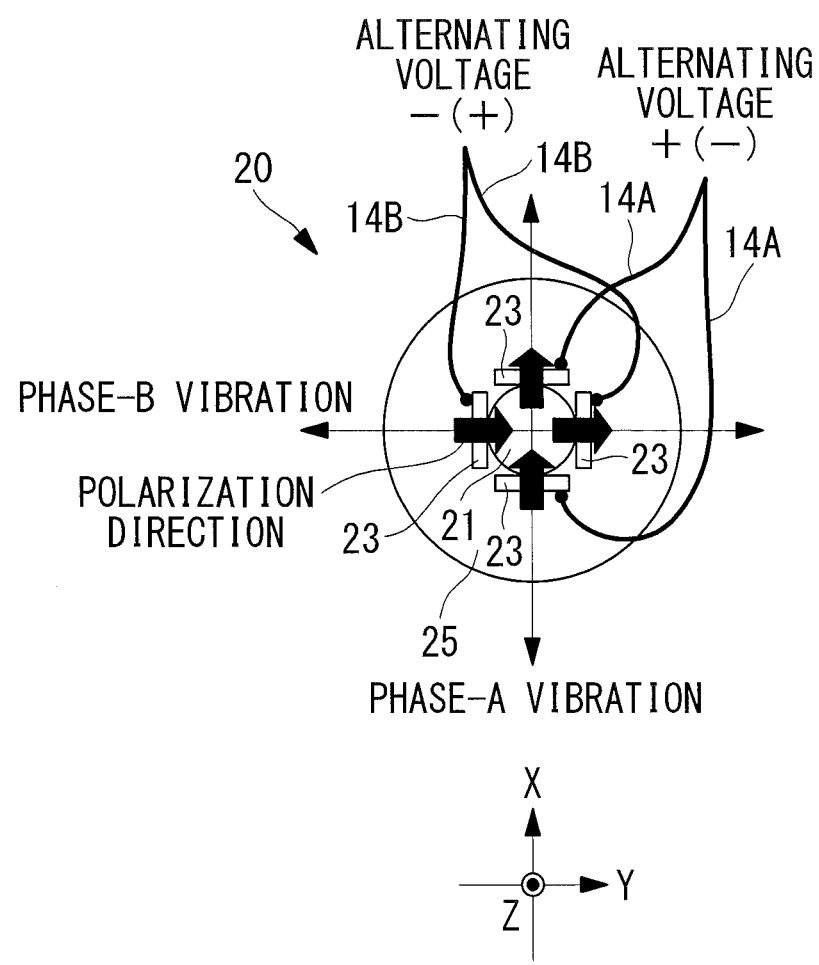
FIG. 4B is a plan view of FIG. 4A, viewed in the longitudinal direction of the illumination optical fiber.

The back-surface electrodes of the piezoelectric elements 23 are electrically joined to the securing part 25 via the adhesives 27, thereby making it possible to use the securing part 25 as a common GND electrode for the four piezoelectric elements 23. In the above-described configuration of this embodiment, areas in which the adhesives 27 are filled to bond the piezoelectric elements 23 to the illumination optical fiber 21 are narrow, and thus only the areas in which the adhesives 27 are filled can serve as a common GND when the piezoelectric elements 23 are driven; therefore, the lead wire 14G connected to a vicinity of the distal end of the optical fiber scanner 20 needs to be pulled toward the base end side of the optical fiber scanner 20. However, according to this modification, as shown in FIGS. 4A and 4B, it is possible to eliminate the need to provide the through hole 25a in the securing part 25 and to directly wire the lead wire 14G to the securing part 25, thus facilitating wiring.

Figure 5:
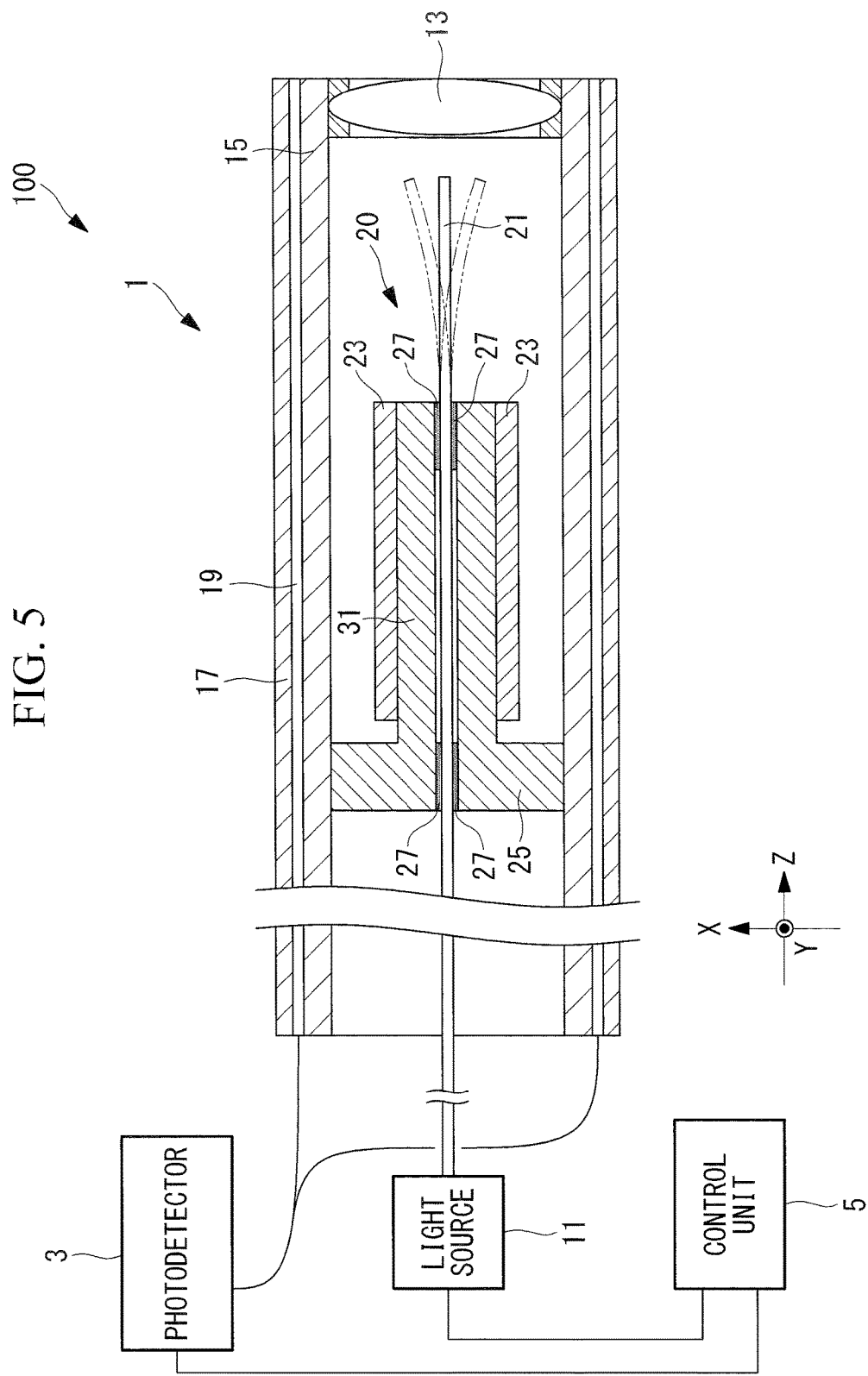
FIG. 5 is a view showing, in outline, the configuration of an optical fiber scanner according to a second modification of the embodiment of the present invention.

In a second modification, as shown in FIG. 5, an intermediate member 31 that is disposed between the piezoelectric elements 23 and the adhesives 27 may be provided.

Figure 6A:
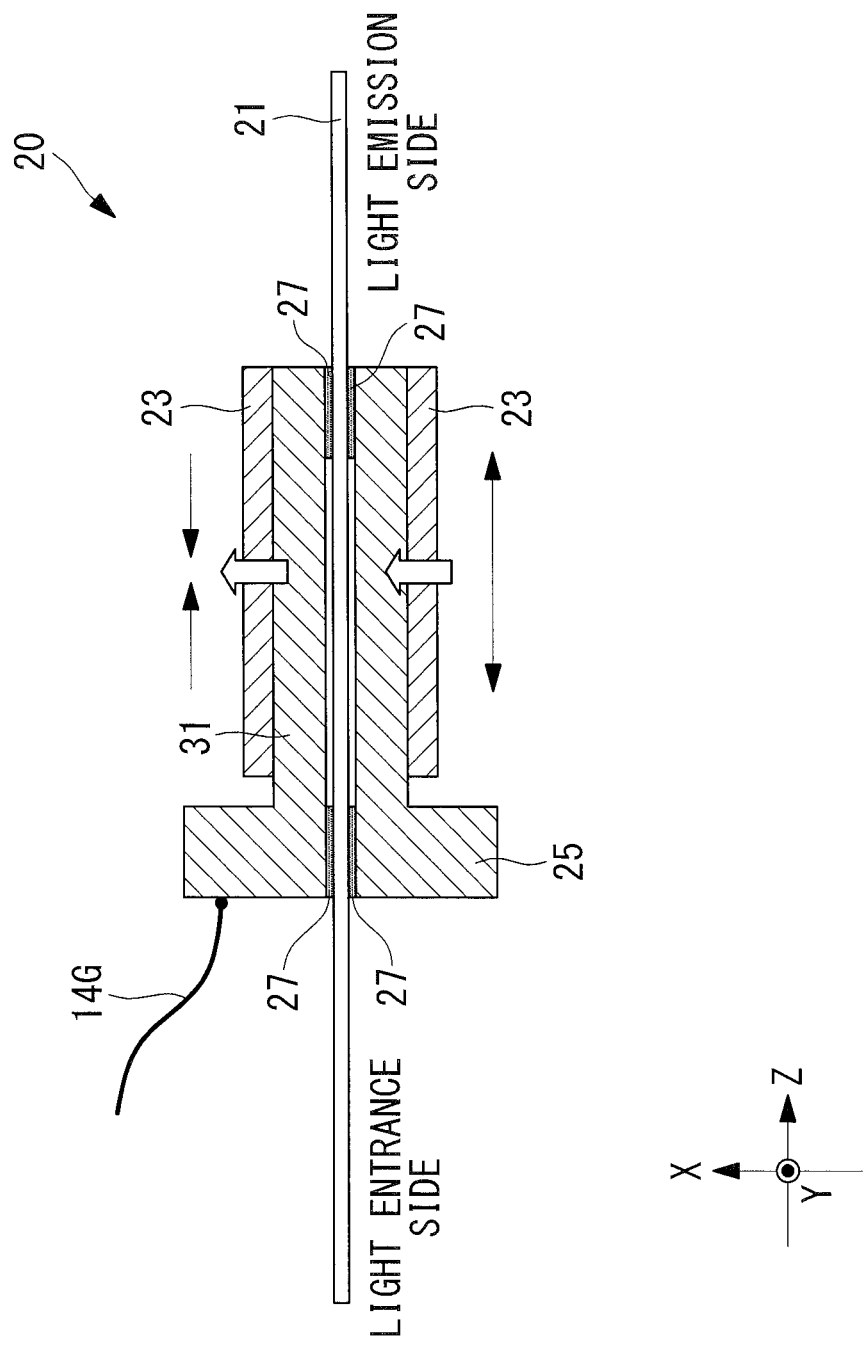
FIG. 6A is a plan view of the optical fiber scanner shown in FIG. 5, viewed in a radial direction of an illumination optical fiber.
Figure 6B:
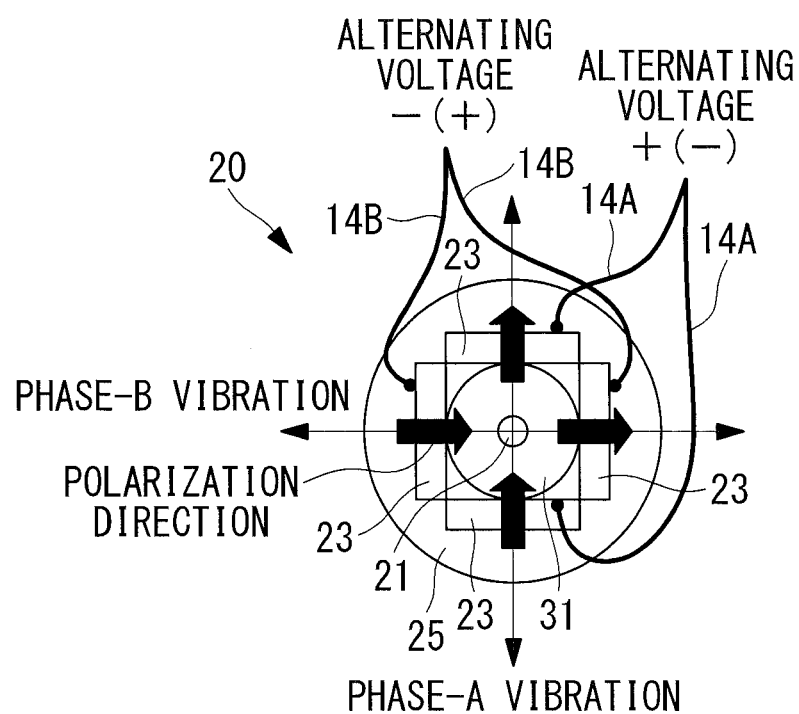
FIG. 6B is a plan view of FIG. 6A, viewed in the longitudinal direction of the illumination optical fiber.

As shown in FIGS. 6A and 6B, the intermediate member 31 may be formed into a cylindrical shape having a through hole for allowing the illumination optical fiber 21 to pass therethrough. Furthermore, the intermediate member 31 may be made from a nickel or copper material, for example, integrally formed with the securing part 25, and formed to have a thickness smaller than the radial thickness dimension of the securing part 25.

In addition to the inner circumferential surface of the securing part 25, at least an end on the inner circumferential surface of the intermediate member 31 closer to the distal end of the illumination optical fiber 21 may be bonded to the illumination optical fiber 21 by means of the adhesive 27.

By doing so, the intermediate member 31 can improve the rigidity of the whole optical fiber scanner 20 and can prevent distortion and wobble of the optical fiber scanner 20 and breaking of the illumination optical fiber 21 due to vibrations.

Figure 7A:
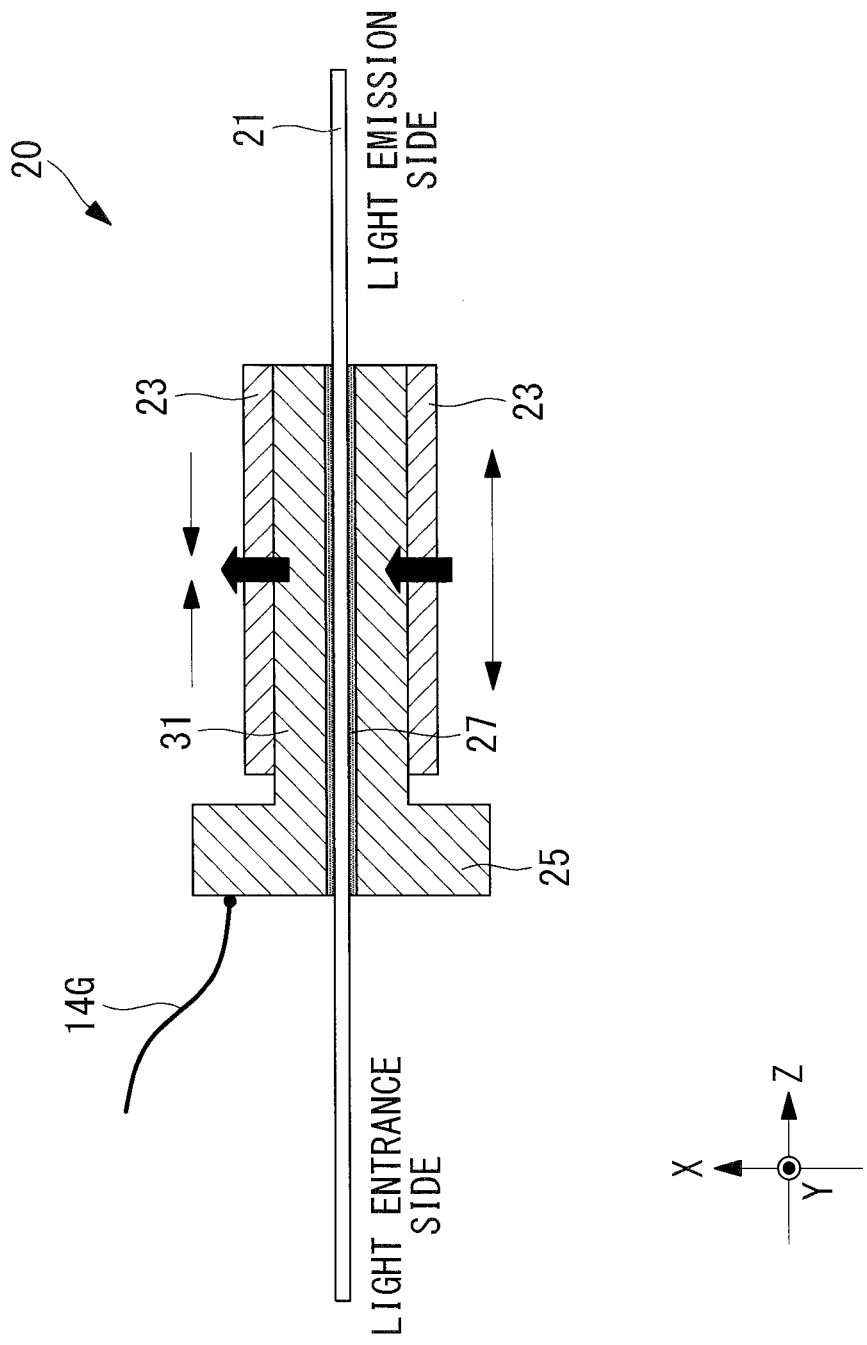
FIG. 7A is a plan view of an optical fiber scanner according to another aspect of the second modification, viewed in a radial direction of the illumination optical fiber.
Figure 7B:
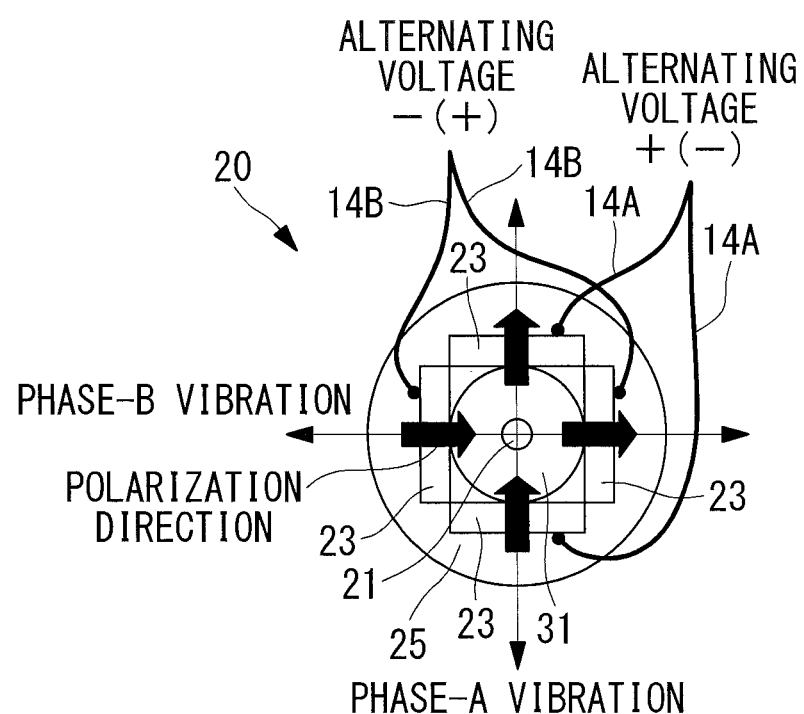
FIG. 7B is a plan view of FIG. 7A, viewed in the longitudinal direction of the illumination optical fiber.

In this modification, as shown in FIGS. 7A and 7B, the entire inner circumferential surface of the intermediate member 31 may be bonded to the side surface of the illumination optical fiber 21 by means of the adhesive 27.

By doing so, it is possible to improve the transfer efficiency of vibrations transferred from the piezoelectric elements 23 to the illumination optical fiber 21.

Figure 8:
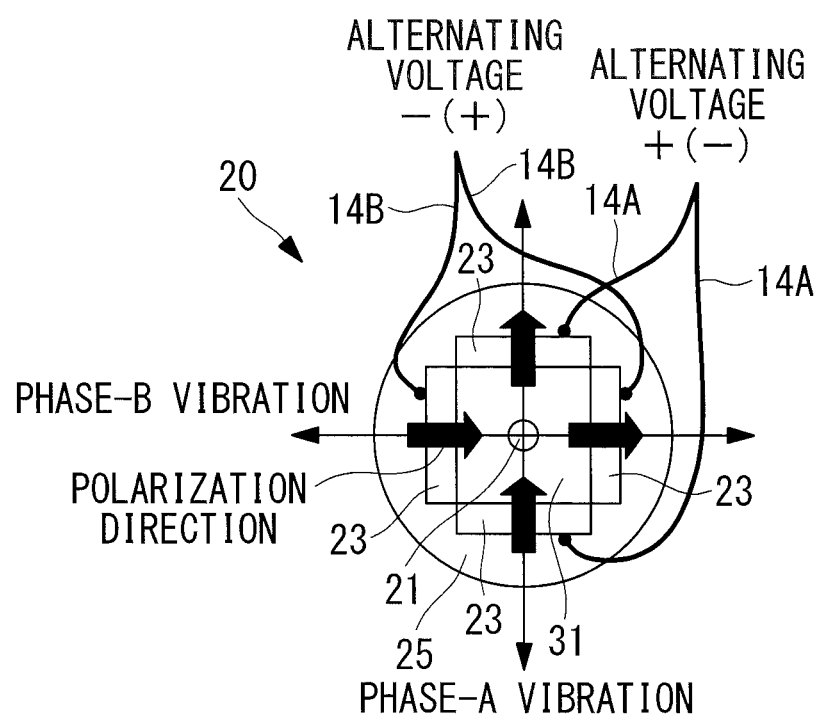
FIG. 8 is a plan view of an optical fiber scanner according to still another aspect of the second modification, viewed in the longitudinal direction of the illumination optical fiber.

In this modification, as shown in FIG. 8, the intermediate member 31 may be formed into a square-pillar shape having a through hole for allowing the illumination optical fiber 21 to pass therethrough.

In this case, the entire front surfaces or the entire back surfaces of the piezoelectric elements 23 are bonded to the four lateral surfaces of the intermediate member 31 by means of the adhesives 27.

Furthermore, as shown in FIG. 6A, in addition to the inner circumferential surface of the securing part 25, at least the end on the inner circumferential surface of the intermediate member 31 closer to the distal end of the illumination optical fiber 21 may be bonded to the illumination optical fiber 21 by means of the adhesive 27. Alternatively, as shown in FIG. 7A, the entire inner circumferential surface of the intermediate member 31 may be bonded to the side surface of the illumination optical fiber 21 by means of the adhesive 27.

By doing so, the piezoelectric elements 23 are secured through surface contact, thus making it possible to improve the ease of assembly and to improve the vibration transfer force.

Figure 9:
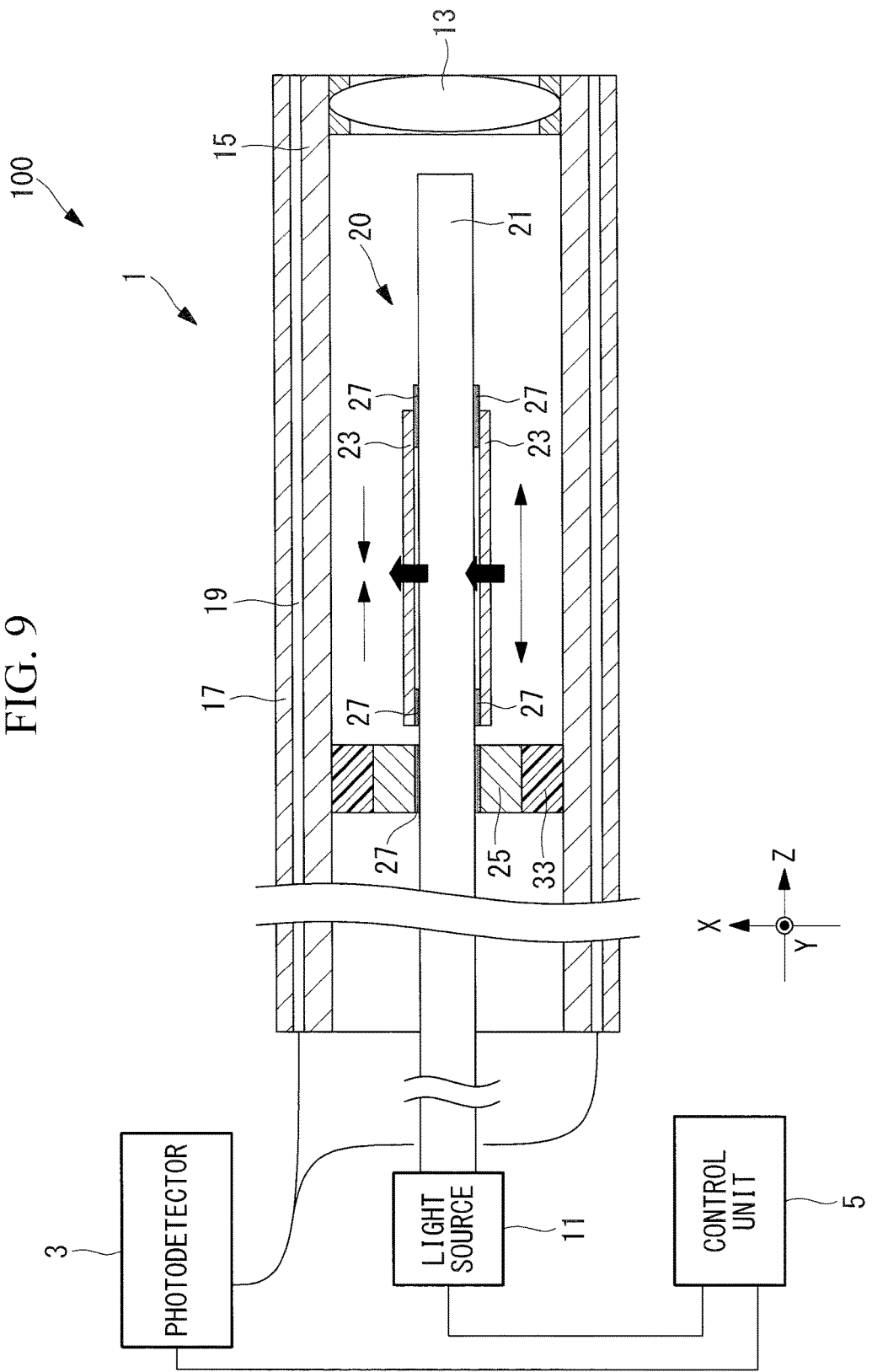
FIG. 9 is a view showing, in outline, the configuration of an observation apparatus according to a third modification of the embodiment of the present invention.
Figure 10:
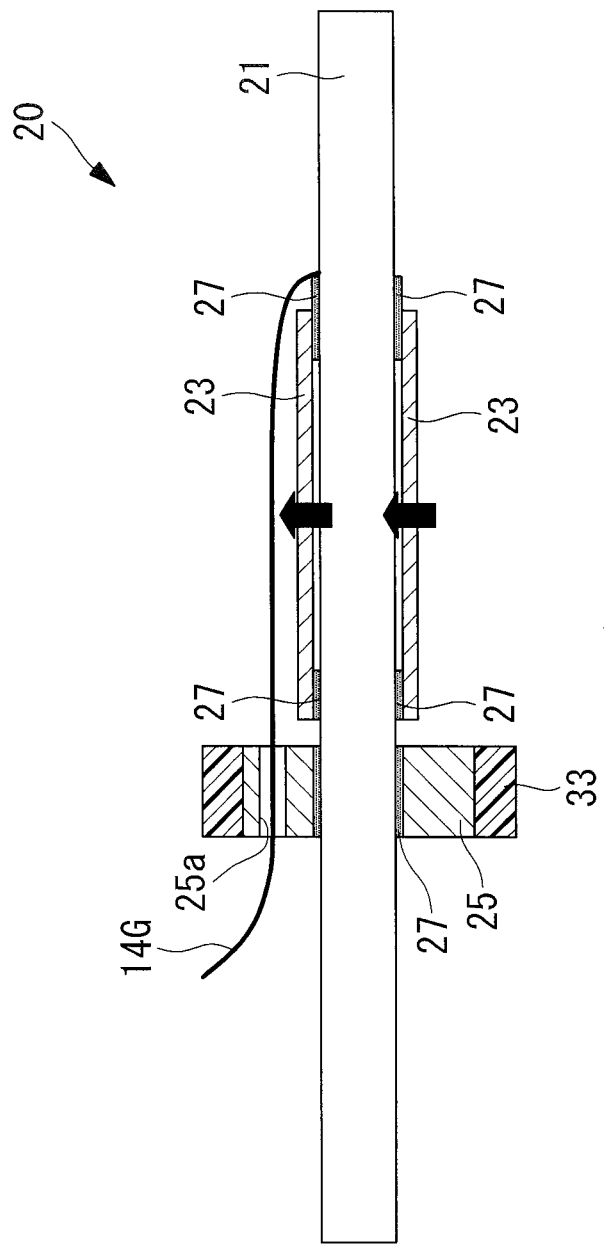
FIG. 10 is a plan view of an optical fiber scanner shown in FIG. 9, viewed in a radial direction of an illumination optical fiber.

In a third modification, as shown in FIGS. 9 and 10, an annular vibration-absorbing member 33 that is made from a resin material having a certain level of strength, such as rubber or silicon, may be provided and disposed between the outer circumferential surface of the securing part 25 and the inner circumferential surface of the external cylinder 15.

By doing so, the vibration-absorbing member 33 can prevent vibrations from leaking from the securing part 25 to the outside. Accordingly, the securing part 25 can absorb radial vibrations generated at the position of the illumination optical fiber 21 closer to the base end than the piezoelectric elements 23 are and can stably secure the illumination optical fiber 21. As a result, the direction in which illumination light is emitted from the illumination optical fiber 21 can be stabilized.

Figure 11:
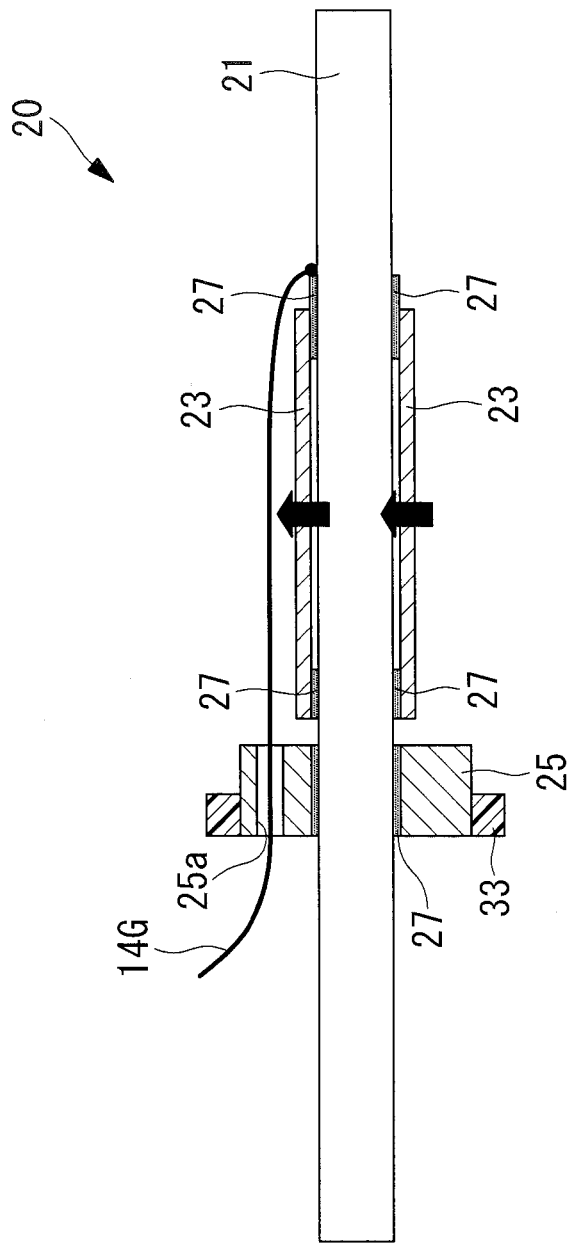
FIG. 11 is a plan view of an optical fiber scanner according to another aspect of the third modification, viewed in a radial direction of the illumination optical fiber.
Figure 12:
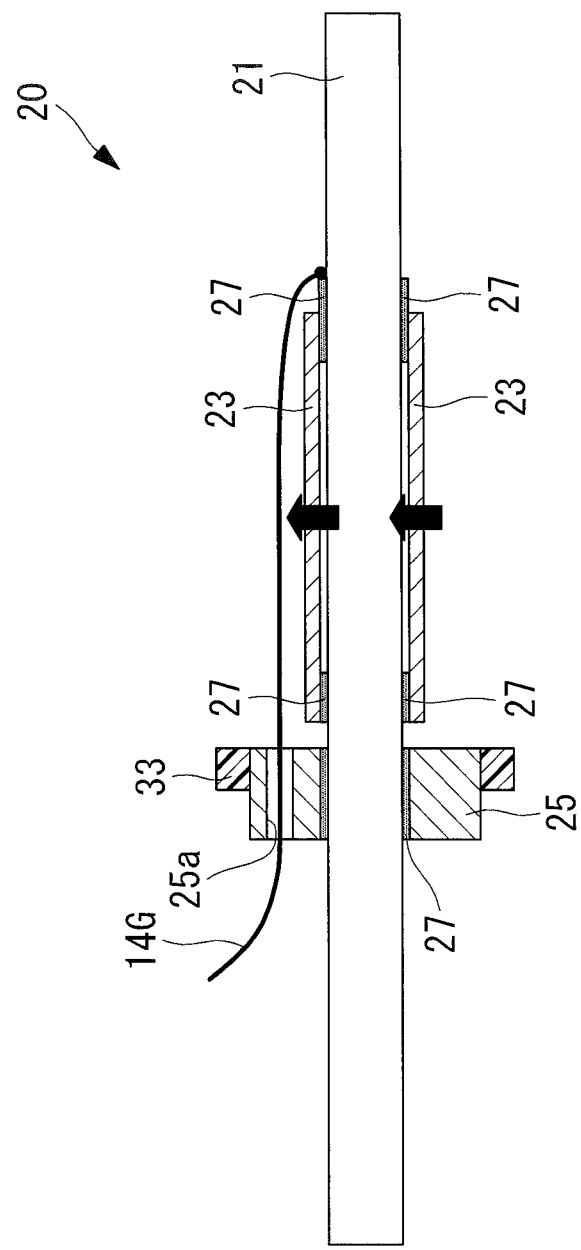
FIG. 12 is a plan view of an optical fiber scanner according to still another aspect of the third modification, viewed in a radial direction of the illumination optical fiber.

In this modification, as shown in FIGS. 9 and 10, the vibration-absorbing member 33 may be provided on the entire outer circumferential surface of the securing part 25. Alternatively, as shown in FIG. 11, the vibration-absorbing member 33 may be partially provided only at a position on the outer circumferential surface of the securing part 25 that is closer to the base end in the axial direction. Alternatively, as shown in FIG. 12, the vibration-absorbing member 33 may be partially provided only at a position on the outer circumferential surface of the securing part 25 that is closer to the distal end in the axial direction.

Figure 13:
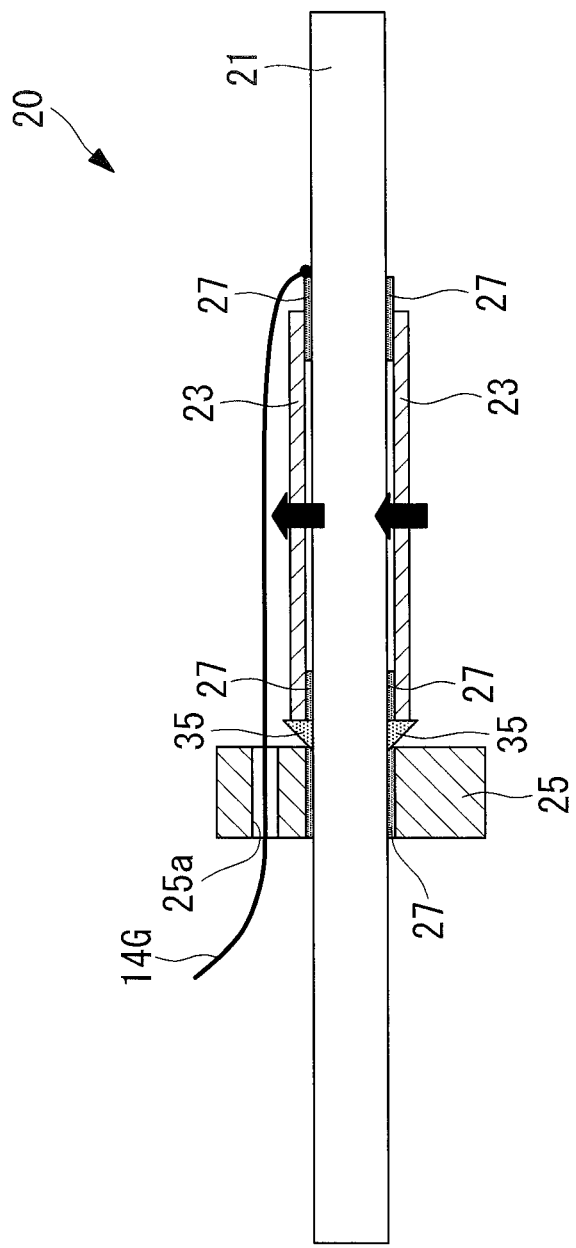
FIG. 13 is a plan view of an optical fiber scanner according to a fourth modification of the embodiment of the present invention, viewed in a radial direction of the illumination optical fiber.

In a fourth modification, as shown in FIG. 13, the space between the piezoelectric elements 23 and the securing part 25 in the longitudinal direction of the illumination optical fiber 21 may be filled with an elastic member 35, such as an adhesive, over the entire circumferential area.

By doing so, a portion of the illumination optical fiber 21 exposed between the piezoelectric elements 23 and the securing part 25 is covered with the elastic member 35, thereby making it possible to improve the rigidity of the optical fiber scanner 20. Accordingly, it is possible to prevent distortion and wobble of the optical fiber scanner 20 and breaking of the illumination optical fiber 21 due to vibrations.

Although the embodiment of the present invention has been described above in detail with reference to the drawings, the specific configuration is not limited to this embodiment, and design changes that do not depart from the scope of the present invention are also encompassed. For example, the present invention is not limited to those applied to the above-described embodiment and modifications thereof and can be applied to an embodiment obtained by appropriately combining these embodiment and modifications thereof. Thus, the present invention is not particularly limited.

In the above-described embodiment, a description has been given of an example configuration in which the four piezoelectric elements 23 are secured to the side surface of the illumination optical fiber 21; however, the number of piezoelectric elements 23 is not limited thereto as long as the piezoelectric elements 23 can vibrate the illumination optical fiber 21. For example, it is possible to adopt a configuration in which only one pair of piezoelectric elements 23 are used or a configuration in which three piezoelectric elements 23 are secured at regular intervals in the circumferential direction of the illumination optical fiber 21. In such cases, with the securing part 25, it is also possible to prevent the shape of vibrations of the piezoelectric elements 23 and vibrations of the illumination optical fiber 21 from becoming unstable and to make the piezoelectric elements 23 easily expand and contract in the longitudinal direction of the illumination optical fiber 21. Accordingly, the illumination optical fiber 21 can be made to stably generate bending vibrations.

The above-described embodiment leads to the following inventions.

According to a first aspect, the present invention provides an optical fiber scanner including: an optical fiber that guides light and emits the light from a distal end thereof; a plurality of piezoelectric elements that are secured on a side surface of the optical fiber, that have polarizations in radial directions of the optical fiber, and that vibrate the optical fiber when an alternating voltage is applied in the polarization directions; and a vibration suppressing part that suppresses vibrations in the radial directions generated at a position of the optical fiber away from the piezoelectric elements toward a base end.

According to this aspect, when an alternating voltage is applied to the piezoelectric elements in their polarization directions, the piezoelectric elements expand and contract in a direction perpendicular to the polarization directions, i.e., in the longitudinal direction of the optical fiber, thereby generating vibrations, and the vibrations are transferred to the optical fiber, thereby vibrating the optical fiber. Accordingly, light emitted from the distal end of the optical fiber can be scanned according to the vibrations.

In this case, the vibration suppressing part suppresses radial vibrations generated at a position of the optical fiber closer to the base end than the piezoelectric elements are, thereby making it possible to prevent the bending vibrations generated in the piezoelectric elements from escaping toward the base end of the optical fiber. Even if the vibrations escape from the piezoelectric elements toward the base end of the optical fiber, it is possible to avoid a situation in which the vibrations return after being changed in shape by being affected in some way. Accordingly, it is possible to prevent the shape of the vibrations of the piezoelectric elements and the vibrations of the optical fiber from becoming unstable.

By forming the space between the piezoelectric elements and the position at which the vibration suppressing part suppresses vibrations of the optical fiber, the piezoelectric elements can be made to easily expand and contract in the longitudinal direction of the optical fiber. Accordingly, a situation in which the vibrations of the piezoelectric elements themselves are disturbed by the vibration suppressing part, thus making it difficult to transfer the vibrations to the optical fiber, can be prevented.

As a result, the optical fiber can be made to stably generate bending vibrations.

In the above-described aspect, it is possible to further include vibration transferring parts that bond at least the vicinities of both ends of each of the piezoelectric elements in the longitudinal direction of the optical fiber to the optical fiber and that transfer vibrations of the piezoelectric elements to the optical fiber.

With this configuration, the vibrations are transferred by the vibration transferring parts to the optical fiber from at least the vicinities of both ends of each of the piezoelectric elements. Accordingly, the vibrations of the piezoelectric elements are efficiently transferred to the optical fiber, thereby making it possible to make the optical fiber generate large bending vibrations in one direction.

In the above-described aspect, the vibration transferring parts may be provided over the entire length of the piezoelectric elements.

With this configuration, it is possible to improve the transfer efficiency of vibrations transferred from the piezoelectric elements to the optical fiber.

In the above-described aspect, it is possible to further include an intermediate member that is integrally formed with the vibration suppressing part, that is disposed between the piezoelectric elements and the vibration transferring parts, and that is made from nickel or copper.

With this configuration, the intermediate member can improve the rigidity of the whole optical fiber scanner and can prevent distortion and wobble of the optical fiber scanner and breaking of the fiber due to vibrations.

In the above-described aspect, it is possible to further include a vibration-absorbing member that absorbs vibrations of the vibration suppressing part and that is made from a resin material.

With this configuration, the vibration-absorbing member can prevent vibrations from leaking from the vibration suppressing part to the outside. Accordingly, the vibration suppressing part stably suppresses radial vibrations generated at the position of the optical fiber closer to the base end than the piezoelectric elements are, thus making it possible to stabilize the direction in which light is emitted from the optical fiber.

According to a second aspect, the present invention provides an illumination system including: one of the above-described optical fiber scanners; a light source that produces light to be guided by the optical fiber; and a condensing lens that condenses light emitted from the optical fiber.

According to this aspect, light produced in the light source can be accurately scanned by the optical fiber scanner, which makes the optical fiber stably generate bending vibrations, and can be radiated onto a desired position of the object by the condensing lens.

According to a third aspect, the present invention provides an observation apparatus including: the above-described illumination system; and a photodetection unit that detects return light returning from an object when the illumination system radiates light onto the object.

According to this aspect, return light returning from a desired region of the object on which light is stably scanned by the illumination system is detected by the photodetection unit. Therefore, it is possible to acquire image information of a desired observation region of the object.

REFERENCE SIGNS LIST 1 illumination system
3 photodetector (photodetection unit)
11 light source
13 condensing lens
20 optical fiber scanner
21 illumination optical fiber (optical fiber)
23 piezoelectric element
25 securing part (vibration suppressing part)
27 adhesive (vibration transferring part)
31 intermediate member
33 vibration-absorbing member
100 observation apparatus

The invention claimed is:

1. An optical fiber scanner comprising:
an optical fiber that guides light and emits the light from a distal end of the optical fiber;
a plurality of piezoelectric elements each secured on a side surface of the optical fiber, each of the plurality of piezoelectric elements having a polarization in a radial direction of the optical fiber, each of the plurality of piezoelectric elements vibrating the optical fiber when an alternating voltage is applied in the polarization directions; and
a vibration suppressing part disposed proximal to a proximal end of the plurality of piezoelectric elements such that the vibration suppressing part suppresses vibrations in the radial direction that are generated at a position of the optical fiber proximal to the proximal end of the plurality of piezoelectric elements.

2. An optical fiber scanner according to claim 1, further comprising an epoxy adhesive that bonds at least each of both ends of each of the plurality of piezoelectric elements in a longitudinal direction of the optical fiber to the optical fiber, and that transfers vibrations of the piezoelectric elements to the optical fiber.

3. An optical fiber scanner according to claim 2, wherein the epoxy adhesive is provided over an entire length in the longitudinal direction of each of the plurality of piezoelectric elements.

4. An optical fiber scanner according to claim 2, further comprising an intermediate member integrally formed with the vibration suppressing part, the intermediate member being disposed between the plurality of piezoelectric elements and the epoxy adhesive, the intermediate member being formed of nickel or copper.

5. An optical fiber scanner according to claim 1, further comprising a vibration-absorbing member that absorbs vibrations of the vibration suppressing part, the vibration-absorbing member being formed of a resin material.

6. An illumination system comprising:
   the optical fiber scanner according to claim 1;
   a light source that produces light to be guided by the optical fiber; and
   a condensing lens that condenses the light emitted from the distal end of the optical fiber.

7. An observation apparatus comprising:
   the illumination system according to claim 6; and
   a photodetection unit that detects return light returning from an object when the illumination system radiates light onto the object.

* * * * *